United States Patent
Shiba et al.

(10) Patent No.: US 8,158,058 B2
(45) Date of Patent: Apr. 17, 2012

(54) AUTOMATIC ANALYZER

(75) Inventors: Masaki Shiba, Hitachinaka (JP);
Masaaki Hanawa, Hitachinaka (JP);
Masaharu Nishida, Hitachinaka (JP);
Hitoshi Otake, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 907 days.

(21) Appl. No.: 10/844,375

(22) Filed: May 13, 2004

(65) Prior Publication Data
US 2004/0253146 A1    Dec. 16, 2004

(30) Foreign Application Priority Data
May 14, 2003   (JP) .................. 2003-135260

(51) Int. Cl.
*G01N 35/04* (2006.01)
(52) U.S. Cl. ................ 422/64; 422/63; 436/43; 436/48
(58) Field of Classification Search .............. 422/63, 422/64, 65, 67; 436/43, 45, 49, 48
See application file for complete search history.

(56) References Cited

U.S. PATENT DOCUMENTS

| | | | | |
|---|---|---|---|---|
| 4,678,752 A | * | 7/1987 | Thorne et al. | 435/287.3 |
| 6,022,746 A | * | 2/2000 | Fritchie et al. | 436/50 |
| 2004/0057872 A1 | * | 3/2004 | Shibuya et al. | 422/64 |
| 2005/0013735 A1 | * | 1/2005 | Gebrian et al. | 422/63 |
| 2005/0014285 A1 | * | 1/2005 | Miller | 436/180 |

FOREIGN PATENT DOCUMENTS

| | | |
|---|---|---|
| EP | 0510686 | 4/1992 |
| EP | 0558212 | 2/1993 |
| EP | 0795754 | 3/1997 |
| EP | 0845674 | 11/1997 |
| JP | 2503751 | 4/1996 |
| JP | 2000-310643 | 11/2000 |
| WO | 94/14073 | 6/2004 |

* cited by examiner

*Primary Examiner* — P. Kathryn Wright
(74) *Attorney, Agent, or Firm* — Mattingly & Malur, PC

(57) ABSTRACT

An automatic analyzer is disclosed that includes a supplementary reagent storage section and reagent bottle transfer mechanism besides an analysis reagent storage section, and that, by managing information on reagents stored in these two reagent storage sections, is capable of automating reagent management such as reagent replacing work, thereby reducing the burden on an operator, minimizing the interruption of an analysis due to reagent registration and reagent replacement, mounting many reagents thereon, and achieving a high throughput.

2 Claims, 4 Drawing Sheets

| PRIORITY | CONDITION |
|---|---|
| 1 | REAGENT INDISPENSABLE TO ANALYSIS START |
| 2 | REAGENT PROVIDED WITH EFFECTIVE CALIBRATION CURVE RESULT |
| 3 | NUMBER OF REMAINING TESTS |
| 4 | EXPIRATION DATE OF REAGENT |

FIG.2

| PRIORITY | CONDITION |
|---|---|
| 1 | REAGENT INDISPENSABLE TO ANALYSIS START |
| 2 | REAGENT PROVIDED WITH EFFECTIVE CALIBRATION CURVE RESULT |
| 3 | NUMBER OF REMAINING TESTS |
| 4 | EXPIRATION DATE OF REAGENT |

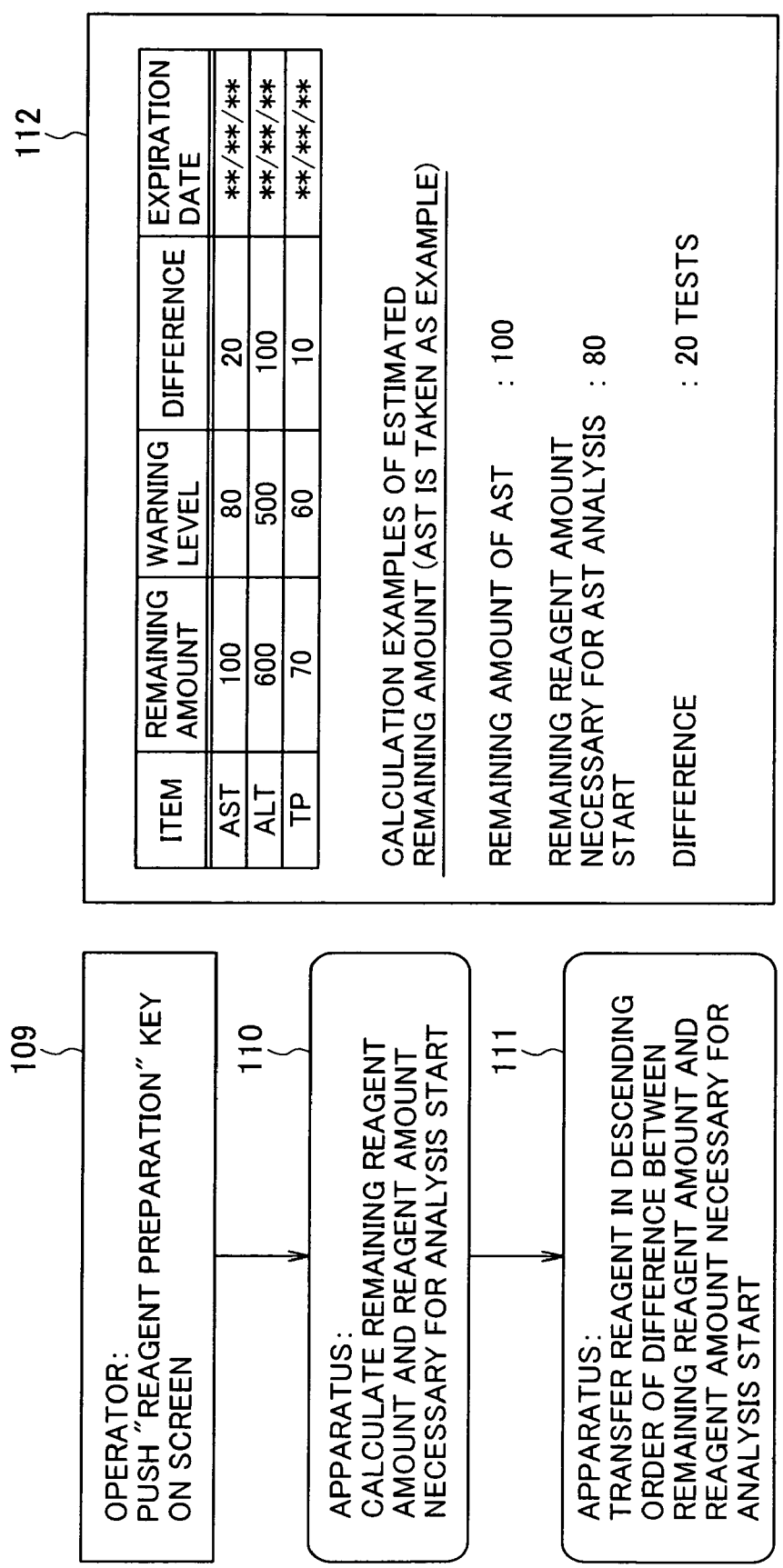

AUTOMATIC ANALYZER

BACKGROUND OF THE INVENTION

1. Field of the Invention

The present invention relates to an automatic analyzer that automatically performs a qualitative/quantitative analysis of a biological sample such as blood, urine, or the like, and more particularly to an automatic analyzer capable of mounting many reagents, and having a high throughput.

2. Description of the Related Art

In the field of automatic analysis, a random access type automatic analyzer, which uses a plurality of reaction lines at random, has been developed, and it has brought about a dramatic improvement in processing capability of analysis. With this improvement, the consumption of reagents has speeded up, and opportunities to replace reagents have increased. Automatic analyzers commonly used are of a type in which a plurality of reagent containers are placed on a rotating disk referred to as a reagent disk, and in which, by rotating the reagent disk, an intended reagent is dispensed from an intended reagent container using a reagent dispensing probe. Among these automatic analyzers, Japanese Registered Utility Model No. 2503751 discloses an automatic analyzer in which, with a view to preventing the interruption of an analysis due to the deficiency of a reagent, a plurality of reagent containers each of which contains a kind of reagent that is to be used a lot are set on the reagent disk so that, when one of the reagent containers becomes deficient in the reagent, the reagent can be dispensed from another of the reagent containers. Also, Japanese Unexamined Patent Application Publication No. 2000-310643 discloses an automatic analyzer in which, at the time of replacing a reagent, information on the expiration date of the reagent after the start of its usage is set, and the elapsed time from the start of the usage of the reagent exceeds its expiration date, an alarm is issued.

SUMMARY OF THE INVENTION

In the conventional art, an operator must perform various work, such as the setting of a reagent before an analysis, the checking of a remaining reagent amount, and the registration of the reagent if the reagent is not subjected to barcode management. Even in the event that the operator uses a system such that an apparatus manages a reagent for the operator once he/she has set the reagent into a reagent storage under a reagent barcode management, if depletion of the reagent occurs in course of analysis, it is necessary for the operator to interrupt the analysis, prepare for a new reagent bottle, set it in the reagent storage, and further perform reagent registration work if required. Moreover, in the case of an apparatus having a plurality of reagent storages in order to increase the amount of mountable reagents, or a system of which the capability of analysis processing varies depending on the disposition of reagents in its reagent storage, the operator must unfavorably manage even the disposition of reagents.

Accordingly, it is an object of the present invention to provide an automatic analyzer that reduces the burden imposed on the operator, such as reagent registration and reagent replacement work, that does not cause a deficiency in reagent during analysis, and that minimize the interruption of an analysis.

In order to achieve the above-described object, the present invention provides an automatic analyzer that includes a first reagent container storage section capable of storing a plurality of reagent containers; a reagent dispensing mechanism for dispensing a reagent from a reagent container stored in the first reagent container storage section; a second reagent container storage section capable of storing a plurality of reagent containers; and a reagent container transfer mechanism capable of transferring a reagent container selected from among reagent containers stored in the second reagent container storage section, to the first reagent container storage section. Herein, based on a preset priority, the reagent container transfer mechanism transfers a reagent container from the second reagent container storage section to the first reagent container storage section.

The above-described preset priority in reagent movement may be determined based on the descending order of the difference between the previously stored amount of a reagent necessary for the start of an analysis and the remaining amount of the reagent present in the reagent storage means.

Also, the priority may be registered by the operator. In this case, it is desirable that a display unit capable of displaying a registration screen be provided.

BRIEF DESCRIPTION OF THE DRAWINGS

FIG. 2 is a table showing the priority of reagent introduction according to the embodiment of the present invention;

FIG. 4 is a flowchart including a calculation example of remaining reagent amount.

DESCRIPTION OF THE PREFERRED EMBODIMENTS

Hereinafter, the automatic analyzer according to an embodiment of the present invention will be described with reference to the accompanying drawings.

Figure 1:
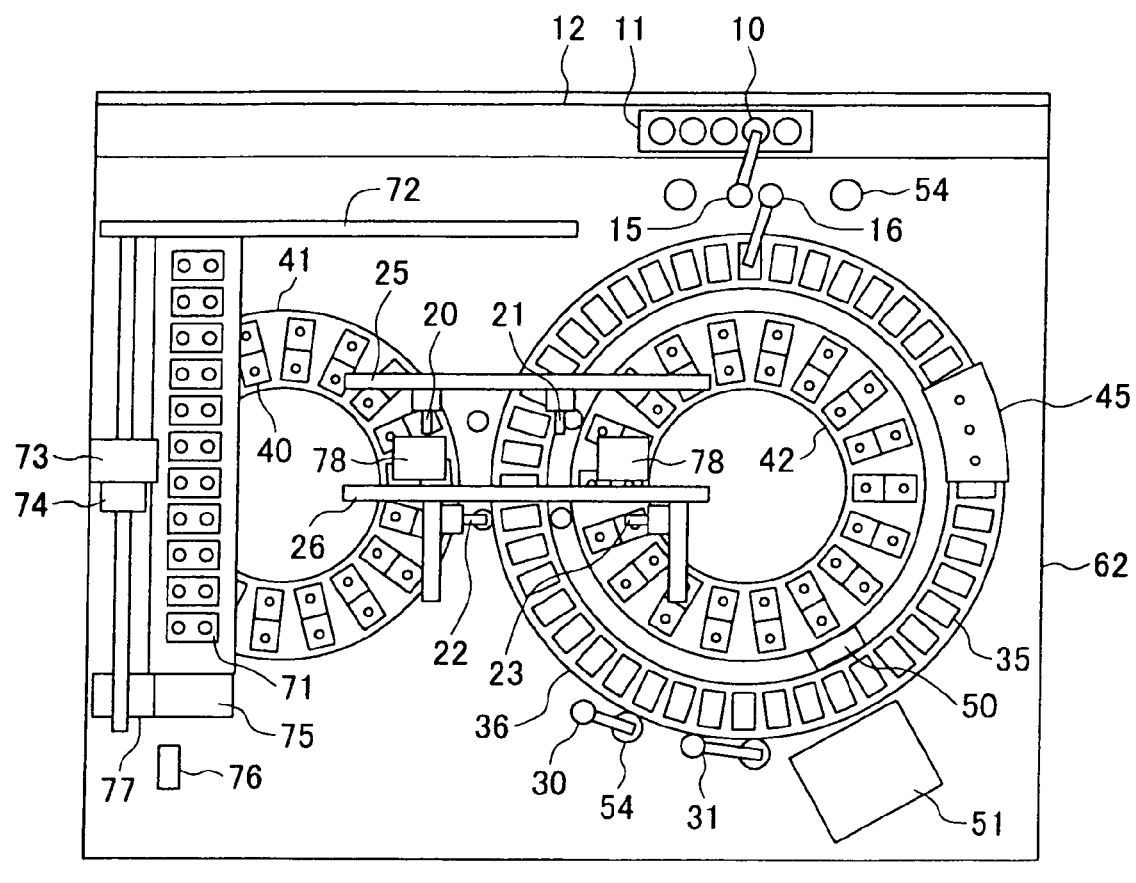
FIG. 1 is a top view of an automatic analyzer according to an embodiment of the present invention.

FIG. 1 is a top view of an automatic analyzer according to the embodiment of the present invention. Reaction vessels 35 are arranged along the circumference of a reaction disk 36 on a cabinet 62. A reagent disk 42 is disposed inside the reaction disk 36, while a reagent disk 41 is disposed outside the reaction disk 36. On each of the reagent disks 41 and 42, a plurality of reagent containers 40 can be mounted along the circumference thereof. One reagent container 40 accommodates two reagents. In the vicinity of the reaction disk 36, there is provided a transfer mechanism 12 for moving a rack 11 having sample containers 10 mounted thereon. Rails 25 and 26 are provided above the reagent disks 41 and 42. To the rail 25 there are provided reagent probes 20 and 21 movable in the direction parallel to the rail 25 and in the up-and-down direction. Also, to the rail 26, there are provided reagent probes 22 and 23 movable in three-axis directions with respect the rail 26. The reagent probes 20, 21, 22, and 23 are connected to respective reagent pumps (not shown). Sample probes 15 and 16 that are each rotatable and movable in the vertical direction are disposed between the reaction vessels 35 and the transfer mechanism 12. The sample probes 15 and 16 are connected to respective sample pumps (not shown). Around the reaction disk 36, there are provided stirrers 30 and 31, a light source 50, detection optical unit 51, a vessel cleaning mechanism 45. The vessel cleaning mechanism 45 is connected to a cleaning pump (not shown). A cleaning port 54 is provided within the operating range of each of the sample probes 15 and 16, the reagent probes 20, 21, 22, and 23, and the stirrers 30 and 31. A supplementary reagent storage 71 is disposed on the reagent disk 41. The supplementary reagent storage 71 can mount a plurality of reagent containers. A rail 72 is provided above the supplementary reagent storage 71.

To the rail 72, there are provided a reagent holding mechanism 73 and a reagent cap opening mechanism 74 movable in the three-directions with respect to the rail 72. A loading gate 75 for reagent container 40 is provided forward of the supplementary reagent storage 71. In the vicinity of the loading gate 75 for reagent container 40, there is provided a barcode reader 76 for reading a reagent barcode. A waste vent 77 for disposing of reagent caps and used reagent containers 40 is disposed in the vicinity of the supplementary reagent storage 71. The sample pump, reagent pump, and cleaning pump, which are not shown, and the detection optical unit 51, reaction vessel 35, reagent disk 41, reagent probes 20, 21, 22, and 23, sample probes 15 and 16, reagent holding mechanism 73, reagent cap opening mechanism 74, reagent container loading gate 75 are each connected to a controller 60.

An analysis procedure will be described below.

Before entering the analysis, firstly the maintenance of the apparatus is performed. In the maintenance, besides the checking of the detection optical unit 51, the cleaning of the reaction vessels 35, and the cleaning of various probes such as the sample probes 15 and 16, the most important matter is the checking of a reagent in each of the reagent containers 40 mounted on the reagent disks 41 and 42. Regarding information on the reagent containers 40, the mounted positions of reagents in the reagent containers 40, lot numbers expiration dates, remaining reagent amounts, and the like are stored in a control computer 200. The operator checks conditions of reagent containers in the reagent disks 41 and 42 by CRT 201 or the like. Reagents of which the remaining amount is slight and which might become empty in course of analysis in a day are set in the loading gate 75 for the reagent container 40. The set reagents have the reagent information thereon read by the barcode reader 76, and then transferred to the supplementary reagent storage 71 by the reagent holding mechanism 73. The reagent information read and the information on the mounted positions of the reagents in the supplementary reagent storage 71 is outputted to the control computer 200.

Figure 3:
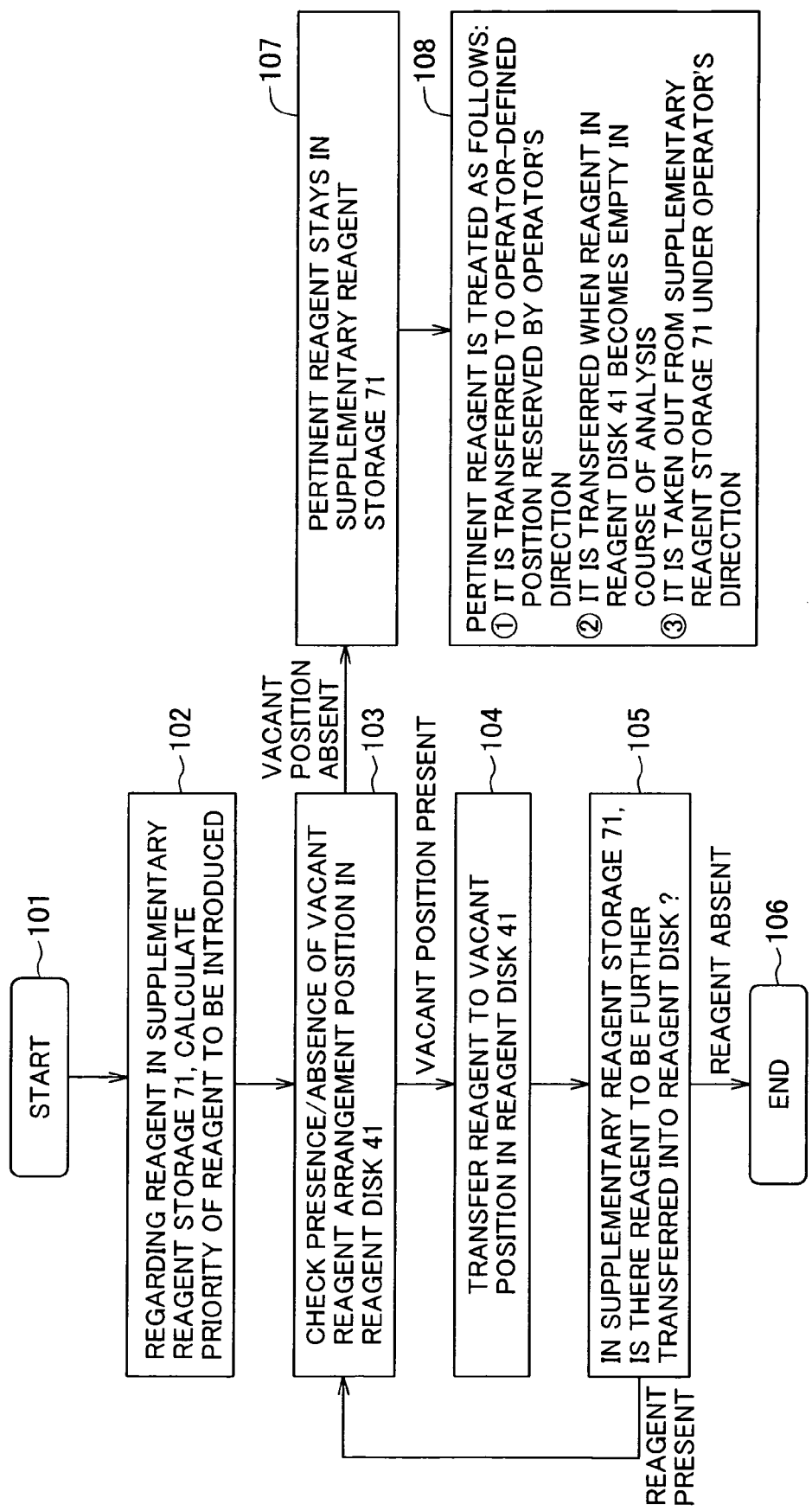
FIG. 3 is a flowchart of the reagent introduction according to the embodiment of the present invention.

Next, a method for transferring a reagent from the supplementary reagent storage 71 to the reagent disk 41 or 42 is shown in FIGS. 2 and 3. The supplementary reagent storage 71 can mount a plurality of reagents. The present apparatus causes the control computer 200 to previously store the reagent and the reagent amount necessary for an analysis start, which are stored in the apparatus in advance. One possible method for causing the control computer 200 to store them is to input them through the control computer 200. Alternatively, the apparatus may cause an external storage medium to store them. Also, in accordance with its frequency of usage, the present apparatus can also automatically change the reagent and reagent amount that are stored, based on the determination of itself. Using the reagent and reagent amount that are stored in advance, the present apparatus introduces the reagent, for example, in accordance with the priority shown in FIG. 2. FIG. 4 shows an example of calculation of the priority of a reagent indispensable to the start of analysis. As shown in FIG. 4, firstly the operator instructs the apparatus to introduce a reagent (step 109). The apparatus calculates the difference between the reagent amount necessary for the analysis start that has been stored in advance and the amount of the reagent that is present in the reagent disks 41 and 42 (steps 110 and 111). FIG. 3 is a flowchart of the introduction of a reagent. The present apparatus calculates the priority of a reagent to be introduced from the supplementary reagent storage 71 after being subjected to instruction to introduce the reagent (step 102). Thereafter, the apparatus checks whether there is a vacant position in the reagent disks 41 and 42 (step 103). If there is no vacant position, the pertinent reagent stays in the supplementary reagent storage 71 until the condition in step 108 shown in FIG. 3 occurs (step 107). Conversely, if there is a vacant position in the reagent arrangement position in the reagent disk 41 or 42 with respect to the condition in step 103, the present apparatus transfers the pertinent reagent from the supplementary reagent storage 71 to the reagent disk 41 or 42 by the reagent holding mechanism 73 (step 104). After completing the transfer, if there is still a reagent to be further transferred to the reagent disk, in the supplementary reagent storage 71 (step 105), the apparatus repeats the flows in step 103 and the steps thereafter. If there is no reagent in the supplementary reagent storage 71, the processing operation is ended (step 106).

The sample container 10 is charged with an object to be examined, such as blood, and after being mounted onto the rack, is conveyed by the transfer mechanism 12. The sample taken by the sample probe 15 is dispensed in a definite amount into reaction vessels 35 arranged on the reaction disk 36, and then a definite amount of regent is dispensed thereinto from the reagent container 40 disposed on the reagent disk 41 or 42, through the reagent probes 21 or 22. This mixture is stirred by the stirrers 30 and 31, and after undergoing a reaction for a definite time, it is measured by the detection optical unit 51. The measurement results are outputted to the control computer 200. If there is a request to further add measurement items, the above-described sampling operation is repeated. Likewise, regarding all samples on the rack 11, the above-described sampling operation is repeated until the sampling with respect to the set measurement items is completed.

As is evident from the foregoing, since the automatic analyzer according to the present invention includes supplementary reagent storage means and reagent bottle transfer means besides analysis reagent storage mean, it is possible to reduce the burden, such as reagent management, imposed on the operator, minimize the interruption of an analysis due to reagent registration and reagent replacement, mount many reagent thereon, and realize a high throughput.

What is claimed is:
1. An automatic analyzer comprising:
a plurality of reagent disks that stores a plurality of reagent containers;
a plurality of reagent probes that dispenses a reagent from a reagent container stored in the reagent disks;
a supplementary reagent storage that stores a plurality of reagent containers;
a rail and reagent holding mechanism that transfers a reagent container selected from among the reagent containers stored in the supplementary reagent storage to the reagent disks; and
a control computer configured to:
(a) check the mounted positions, lot numbers, expiration dates, and remaining reagent amounts of the reagent in the reagent containers mounted on the plurality of reagent disks;
(b) detect whether there is at least one vacant position in the reagent disks where no reagent container resides;
(c) transfer a reagent container meeting a highest priority condition to the detected vacant position in the reagents disks using the rail and reagent holding mechanism; and
(d) transfer a reagent container meeting the next highest priority condition, to a detected next vacant position using the rail and reagent holding mechanism, and repeating this step (d),
wherein the controller determines the highest priority condition where the reagent container is preferentially transferred to one of the reagent disks based on the highest priority condition (i) to lowest priority condition (iv):

(i) a first priority condition where the reagent in the supplementary storage reagent is determined to be indispensable to analysis, and, if more than one reagent container on the supplementary reagent storage meets the first priority condition proceed to item (ii), (ii) a second priority condition wherein the reagent container storing the reagent is selected based where supplementary storage reagent container has the same lot number or used for analyzing the same analysis item as the reagent container mounted on the plurality of reagent disks, and if more than one reagent container on the supplementary reagent storage meets the second priority condition proceed to item (iii), (iii) a third priority condition wherein the reagent container storing the reagent is selected based on the of a number of tests for which the reagent can be used in analysis, and if more than one reagent container on the supplementary reagent storage meets the third priority condition proceed to item (iv), and (iv) a fourth priority condition wherein the reagent container storing the reagent is selected based on an expiration date of the reagent when the reagent can be used in analysis.

2. The automatic analyzer according to claims 1, wherein when the control computer detects that there is no vacant position in the reagent disks, the reagent container meeting the highest priority condition (i) to (iv) is caused to wait in the supplementary reagent storage, and wherein, once the control computer has detected the occurrence of a vacant position in one of the reagent disks, the reagent container meeting the highest priority condition (i) to (iv) is transferred to one of the reagent disks using the rail and reagent holding mechanism.

* * * * *